(12) United States Patent
Viswanathan et al.

(10) Patent No.: US 10,435,503 B2
(45) Date of Patent: Oct. 8, 2019

(54) COMPOSITIONS FOR POLYURETHANE APPLICATIONS

(71) Applicant: Hexion Inc., Columbus, OH (US)

(72) Inventors: Ganapathy Viswanathan, Louisville, KY (US); Anthony Maiorana, Louisville, KY (US); Stephan Schröter, Essen (DE); Pravin Kukkala, Louisville, KY (US)

(73) Assignee: HEXION INC., Columbus, OH (US)

( * ) Notice: Subject to any disclaimer, the term of this patent is extended or adjusted under 35 U.S.C. 154(b) by 0 days.

(21) Appl. No.: 15/713,583

(22) Filed: Sep. 22, 2017

(65) Prior Publication Data

US 2019/0092897 A1 Mar. 28, 2019

(51) Int. Cl.

| | |
|---|---|
| C08K 3/01 | (2018.01) |
| C08G 18/76 | (2006.01) |
| C08G 18/73 | (2006.01) |
| C08G 18/10 | (2006.01) |
| C07C 251/64 | (2006.01) |
| C08K 5/3462 | (2006.01) |
| C08K 5/3492 | (2006.01) |
| C08K 3/016 | (2018.01) |
| C08L 75/04 | (2006.01) |
| C08G 18/54 | (2006.01) |
| C08G 18/65 | (2006.01) |
| C08G 18/75 | (2006.01) |
| C08G 18/79 | (2006.01) |
| C08G 18/80 | (2006.01) |
| C08J 9/14 | (2006.01) |
| C08G 18/18 | (2006.01) |
| C08G 18/20 | (2006.01) |
| C08G 18/40 | (2006.01) |
| C08K 5/49 | (2006.01) |
| C08G 101/00 | (2006.01) |

(52) U.S. Cl.
CPC ........ *C08G 18/7621* (2013.01); *C07C 251/64* (2013.01); *C08G 18/10* (2013.01); *C08G 18/1833* (2013.01); *C08G 18/2081* (2013.01); *C08G 18/4027* (2013.01); *C08G 18/544* (2013.01); *C08G 18/6511* (2013.01); *C08G 18/73* (2013.01); *C08G 18/755* (2013.01); *C08G 18/7664* (2013.01); *C08G 18/7671* (2013.01); *C08G 18/791* (2013.01); *C08G 18/80* (2013.01); *C08J 9/141* (2013.01); *C08K 3/016* (2018.01); *C08K 5/3462* (2013.01); *C08K 5/34922* (2013.01); *C08K 5/49* (2013.01); *C08L 75/04* (2013.01); *C08G 2101/00* (2013.01); *C08G 2101/005* (2013.01); *C08G 2101/0008* (2013.01); *C08G 2101/0025* (2013.01); *C08G 2101/0083* (2013.01); *C08G 2120/00* (2013.01); *C08G 2170/20* (2013.01); *C08G 2190/00* (2013.01); *C08G 2350/00* (2013.01); *C08G 2380/00* (2013.01); *C08G 2410/00* (2013.01)

(58) Field of Classification Search
USPC .......................................................... 528/52
See application file for complete search history.

(56) References Cited

U.S. PATENT DOCUMENTS

| | | |
|---|---|---|
| 2,448,767 A | 9/1948 | Carlson |
| 2,987,555 A | 6/1961 | Davis |
| 3,265,668 A | 8/1966 | Rostyslaw et al. |
| 3,328,321 A | 6/1967 | Wismer et al. |
| 3,399,151 A | 8/1968 | Kaiser |
| 3,470,118 A | 9/1969 | Forster |
| 4,032,514 A | 6/1977 | Burriks et al. |
| 4,060,501 A | 11/1977 | Naylor et al. |
| 4,067,843 A | 1/1978 | Annis et al. |
| 4,087,480 A | 5/1978 | Takahashi et al. |
| 4,107,229 A | 8/1978 | Tideswell et al. |
| 4,261,922 A | 4/1981 | Kem |
| 4,310,707 A | 1/1982 | Strege |
| 4,419,477 A | 12/1983 | Saeki et al. |
| 4,474,951 A | 10/1984 | Pope |
| 4,483,941 A | 11/1984 | Yang |
| 4,500,655 A | 2/1985 | Brennan |
| 4,680,054 A | 7/1987 | TakeMatsu et al. |
| 5,059,670 A | 10/1991 | Harris |
| 5,059,723 A | 10/1991 | Dressler |
| 5,104,987 A | 4/1992 | King |
| 5,272,226 A | 12/1993 | Lancaster et al. |
| 5,457,140 A | 10/1995 | Nunez et al. |
| 5,605,757 A | 2/1997 | Klett |
| 5,679,871 A | 10/1997 | Nava |
| 5,686,379 A | 11/1997 | Imanaka et al. |

(Continued)

FOREIGN PATENT DOCUMENTS

| | | |
|---|---|---|
| EP | 0212214 | 3/1987 |
| GB | 758249 | 10/1956 |

(Continued)

OTHER PUBLICATIONS

Borkovec, A. et al., Derivaties of Melamine, Entomology Research Div., US Dept. of Agriculture, Insent Chemosterilants vol. 10, pp. 457-461, Maryland, May 1967.

*Primary Examiner* — Terressa Boykin

(57) ABSTRACT

A process comprising, consisting of, or consisting essentially of: foaming a reaction mixture containing at least one polyisocyanate and an isocyanate-reactive compound comprising at least one alkoxylated triazine-arylhydroxy-aldehyde condensate composition wherein the alkoxylated triazine-arylhydroxy-aldehyde condensate composition is a reaction product of a triazine-arylhydroxy-aldehyde condensate and at least one alkylene carbonate, is disclosed.

19 Claims, No Drawings

(56) References Cited

U.S. PATENT DOCUMENTS

| | | |
|---|---|---|
| 6,229,054 B1 | 5/2001 | Dal et al. |
| 6,498,278 B1 | 12/2002 | Clements et al. |
| 6,586,607 B1 | 7/2003 | Durairaj et al. |
| 6,605,354 B1 | 8/2003 | Gerber |
| 7,767,778 B2 | 8/2010 | Rawlins et al. |
| 9,133,377 B2 | 9/2015 | Bremont et al. |
| 9,228,040 B2 | 1/2016 | Pinto et al. |
| 9,249,251 B2 | 2/2016 | Viswanathan et al. |
| 1,011,890 A1 | 11/2018 | Viswanathan et al. |
| 2003/0045667 A1 | 3/2003 | Ratzsch et al. |
| 2005/0192422 A1 | 9/2005 | Da Costa et al. |
| 2012/0009407 A1 | 1/2012 | Peeler et al. |
| 2016/0010823 A1 | 1/2016 | Seyrlehner et al. |
| 2016/0108231 A1 | 4/2016 | Aube et al. |
| 2017/0306077 A1 | 10/2017 | Chaffanjon et al. |

FOREIGN PATENT DOCUMENTS

| | | |
|---|---|---|
| GB | 775459 | 5/1957 |
| GB | 934629 | 8/1963 |
| GB | 1029033 | 5/1966 |
| GB | 2350616 | 12/2000 |
| JP | 2008063452 | 3/2008 |
| WO | WO2011029711 | 3/2011 |
| WO | WO2012016803 | 2/2012 |
| WO | WO2015104048 | 7/2015 |
| WO | WO2017160362 | 9/2017 |

COMPOSITIONS FOR POLYURETHANE APPLICATIONS

FIELD OF THE INVENTION

This invention relates to processes for making polymers from polyisocyanates and isocyanate reactive materials. In particular, this invention relates to alkoxylated triazine-arylhydroxy-aldehyde condensate compositions useful as isocyanate reactive materials.

BACKGROUND OF THE INVENTION

Aromatic polyols are used as cross-linkers for isocyanates and isocyanurates that go into polyurethane and polyisocyanurate-based polymers. The largest end use for aromatic polyols is in applications where insulation, flammability, and structural performance are most important.

There is an increasing demand for better performing rigid polyurethane foams that have particular flammability specifications and acceptable physical properties. It is known that when typical rigid polyurethane foams, particularly spray foams, are formed in thicknesses of greater than about 2 inches, such foams are subject to internal scorching due to high exotherm temperatures resulting from reactions of certain isocyanates and polyols. Internal scorching not only degrades the physical properties of the rigid polyurethane foams rendering them unsuitable for most applications but also has the potential to cause other problems related to flammability. In addition, these typical rigid polyurethane foams are flammable and vulnerable to burning and smoking, all of which are undesirable.

To reduce scorch, decrease flammability and smoking, many rigid polyurethane foams include high levels of halogenated flame retardants. Although halogenated flame retardants are inexpensive, they have been linked to environmental concerns. Accordingly, there remains an opportunity to develop rigid polyurethane foam that has a minimum amount of halogenated flame retardants or eliminate the need to have an additional flame retardant that resists scorching, burning, and smoking, while simultaneously having acceptable physical properties.

Novolacs are known to the polyurethane industry as aromatic polyols that typically go into rigid polyurethane and polyisocyanurate foam applications. The novolac polyol is said to promote intumescence (i.e., swelling) of the rigid polyurethane foam, promotes char, decreases scorch, and decreases flammability of the foam. The novolac polyol is also thought to react with isocyanates more quickly than the isocyanates react with water thereby increasing production speed, reducing cost, and allowing the rigid polyurethane foam prepared from a novolac polyol to be used in a wide variety of applications, especially those that require fast foaming times.

While novolacs improve the flame retardancy of the polyurethane formulations and offer rigidity to the foam, these materials have drawbacks. The main challenges are the processing difficulty due to high viscosity.

Once the polyol is mixed with the isocyanates, the gel time is typically 10-25 seconds so the novolac has to mix into the system quickly, which can be a challenge due to the inherent viscosity. In addition, the urethane bond formed by the reaction of aromatic polyol and isocyanate is reversible at certain temperatures where the aliphatic polyol replaces the aromatic polyol. These factors can lead to decreased performance and difficulties in processing. While aromatic polyols offer end use benefits in polyurethanes such as flame resistance and scorch resistance they are difficult to employ in existing processes due to high viscosity and stability of the final product.

The current polyurethane formulations for applications such as rigid foam require multifunctional polyols as isocyanate reactive chemicals. The common ones are carbohydrate-based polyols, which are not very effective when it comes to flame resistance.

Thus, there is a need for aromatic polyols having decreased viscosity that will have minimal tendency to unzip in the presence of other polyols, that will increase cure efficiency, resulting in a foam with improved flammability, insulation, and mechanical characteristics compared to foams prepared with conventional polyols.

SUMMARY OF THE INVENTION

In one broad embodiment of the present invention, there is disclosed a process comprising, consisting of, or consisting essentially of: forming a reaction mixture containing at least one polyisocyanate and an isocyanate-reactive compound comprising at least one alkoxylated triazine-arylhydroxy-aldehyde condensate composition wherein the alkoxylated triazine-arylhydroxy-aldehyde condensate composition is a reaction product of a triazine-arylhydroxy-aldehyde condensate and at least one alkylene carbonate.

DETAILED DESCRIPTION OF THE INVENTION

Embodiments of the invention are directed to alkoxylated triazine-arylhydroxy-aldehyde condensates, methods for making the alkoxylated triazine-arylhydroxy-aldehyde condensates, and the use of alkoxylated triazine-arylhydroxy-aldehyde condensates in the manufacture of polyurethane and polyisocyanurate resins.

An alkoxylated triazine-arylhydroxy-aldehyde condensate is formed by reacting a triazine-arylhydroxy-aldehyde condensate with an alkylene carbonate.

Any suitable triazine-arylhydroxy-aldehyde condensate can be used in the reaction with the alkylene carbonate. In various embodiments, the triazine-arylhydroxy-aldehyde condensate is formed from a reaction mixture of a triazine monomer, an arylhydroxy monomer, and an aldehyde monomer. In various embodiments, the triazine-arylhydroxy-aldehyde condensate is a novolac.

The triazine monomer can be a triazine compound or a triazine derivative. An example of a triazine compound is melamine and an example of a triazine derivative is a melamine derivative.

Suitable compounds that can be used as the triazine monomer include compounds selected from the group of aminotriazine, 4-methyl-1,3,5-triazine-2-amine, 2-amino-4,6-dimethyl-1,3,5-triazine, melamine, hexamethoxymethylmelamine, hexamethylolmelamine, guanamine, acetoguanamine, propioguanamine, butyroguanamine, benzoguanamine, vinylguanamine, 6-(hydroxyphenyl)-2,4-diamino-1,3,5-triazine, and combinations thereof.

The arylhydroxy monomer can be any suitable aromatic monomer with one or more hydroxyl groups per molecule, such as a monohydroxy, dihydroxy or a trihydroxy benzene. They can be mononuclear or binuclear. In various embodiments, the arylhydroxy monomer is a phenol monomer compound. Phenol monomer compounds having at least one ortho or para position available for bonding are preferred compounds. The phenol monomer compound can be an unsubstituted or substituted compound, for example, with an alkyl group, a phenyl group, a hydroxybenzene group, an alkoxy group, and combinations and subsets thereof. The phenol monomer compound can also include compounds having up to about 15 carbon atoms such as up to about 8 carbon atoms. Examples of such arylhydroxy monomers include, but are not limited to phenol, cresols, xylenols, resorcinol, catechol, hydroquinone, naphthols, biphenols, bisphenols, phloroglucinol, pyrogallol or their derivatives.

The aldehyde monomer includes compounds having one or more aldehyde functional groups (—CHO) and any compounds yielding aldehydes. The aldehyde monomer can be represented by the formula R—CHO, and R can be an aliphatic or aromatic organic functional group. The aldehyde monomer can be a dialdehyde such as glyoxal. Suitable aldehydes include, but are not limited to compounds selected from the group of formaldehyde, paraformaldehyde, acetaldehyde, i-butyraldehyde (isobutyraldehyde), benzaldehyde, acrolein, crotonaldehyde, salicylaldehyde, 4-hydroxybenzaldehyde, furaldehyde, pyrrolaldehyde, cinnamaldehyde, trioxymethylene, paraldehyde, terephthaldialdehyde, glyoxal, glutaraldehyde and combinations thereof.

The triazine-arylhydroxy-aldehyde condensate can be comprised of a variety of triazine, arylhydroxy, and aldehyde combinations. In various embodiments, the condensate is a melamine, phenol, and formaldehyde novolac. Further details about the triazine-arylhydroxy-aldehyde condensate and its preparation can be found in U.S. Pat. Nos. 6,239,248 and 9,249,251, which are both herein incorporated by reference.

The triazine-arylhydroxy-aldehyde condensate is reacted with at least one alkylene carbonate to form the alkoxylated triazine-arylhydroxy-aldehyde condensate.

The alkylene carbonate can be a variety of alkylene carbonates. Mixtures of alkylene carbonates can also be used. The general structure of an alkylene carbonate is represented by Formula I, below:

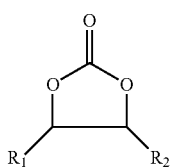

Formula I

In Formula I, $R_1$ and $R_2$ are each independently a hydrogen atom, an alkyl group having 1 to 4 carbon atoms, a vinyl group, or an alkyl group with 1 to 4 carbon atoms containing a hydroxyl group.

The alkylene carbonate can also be a six-membered structure, as represented by Formula II, below:

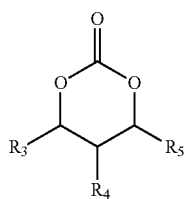

Formula II

In Formula II, $R_3$, $R_4$, and $R_5$ are each independently a hydrogen atom, an alkyl group having 1 to 4 carbon atoms, a vinyl group, or an alkyl group with 1 to 4 carbon atoms containing a hydroxyl group.

In the descriptions of the alkoxylated triazine-arylhydroxy-aldehyde condensate composition below, $R_1$ and $R_2$ in the product structure generally correspond to the $R_1$ and $R_2$ groups of Formula I. In various embodiments, where a composition having the structure of Formula II is used to make the composition, $R_3$, $R_4$, and/or $R_5$ groups are substituted for the $R_1$ and $R_2$ groups. In various embodiments, the alkylene carbonate can be selected from the group consisting of ethylene carbonate, propylene carbonate, and mixtures thereof.

The triazine-arylhydroxy-aldehyde condensate is reacted with at least one alkylene carbonate to form an alkoxylated triazine-arylhydroxy-aldehyde condensate. In various embodiments, reaction conditions can include a reaction temperature in the range of from 50° C. to 270° C. Any and all temperatures within the range of 50° C. to 270° C. are incorporated herein and disclosed herein; for example, the reaction temperature can be from 100° C. to 200° C., from 140° C. to 180° C., or from 160° C. to 175° C. The reaction conditions can also include a reaction pressure in the range of from 0.01 bar to 100 bar. Any and all pressures within the range of from 0.01 bar to 100 bar are included herein and disclosed herein; for example, the reaction pressure can be from 0.1 bar to 50 bar, from 0.5 bar to 20 bar, or from 1 bar to 10 bar. The components can be added together in any suitable manner. For example, the reaction can take place in a batch system, a continuous system, a semi-batch system, or a semi-continuous system. In various embodiments, the alkylene carbonate can be added slowly to molten triazine-arylhydroxy-aldehyde condensate and then reacted until $CO_2$ evolution has ceased.

Optionally, the reaction between the triazine-arylhydroxy-aldehyde condensate and the alkylene carbonate can take place in the presence of a catalyst. Examples of catalysts that can be used include, but are not limited to sodium hydroxide, potassium hydroxide, lithium hydroxide, ammonium hydroxide, magnesium hydroxide, calcium hydroxide, barium hydroxide, sodium carbonate, sodium bicarbonate, potassium carbonate, potassium bicarbonate, potassium phosphate, sodium phosphate, and lithium phosphate. If necessary, an organic acid such as oxalic acid, formic acid, acetic acid, trifluoroacetic acid, methane sulfonic acid, salicylic acid, or p-toluenesulfonic acid can be used to neutralize the reaction mixture.

In various embodiments, the alkoxylated triazine-arylhydroxy-aldehyde condensate compound can be represented by Formula III below.

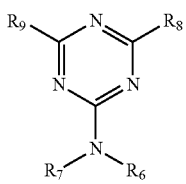

Formula III

The $R_6$ functional group is represented by Formula IV or Formula V. The $R_7$ functional group of Formula III can be a hydrogen atom or represented by Formula IV or Formula VI. $R_8$ and $R_9$ can each independently be a hydrogen atom, an alkyl group with 1 to 10 carbon atoms, a vinyl group, a phenyl group, a hydroxyphenyl group, NH(Formula VI), —N(Formula VI)$_2$, —NH(Formula IV), —N(Formula IV)(Formula VI), —N(Formula IV)$_2$, —NH(Formula V), —N(Formula V)(Formula VI), —N(Formula V)$_2$, NH(Formula VII), —N(Formula VI)(Formula VII), —N(Formula VII)$_2$, or —NH$_2$.

The structures of Formulas IV, V, VI, and VII are depicted below.

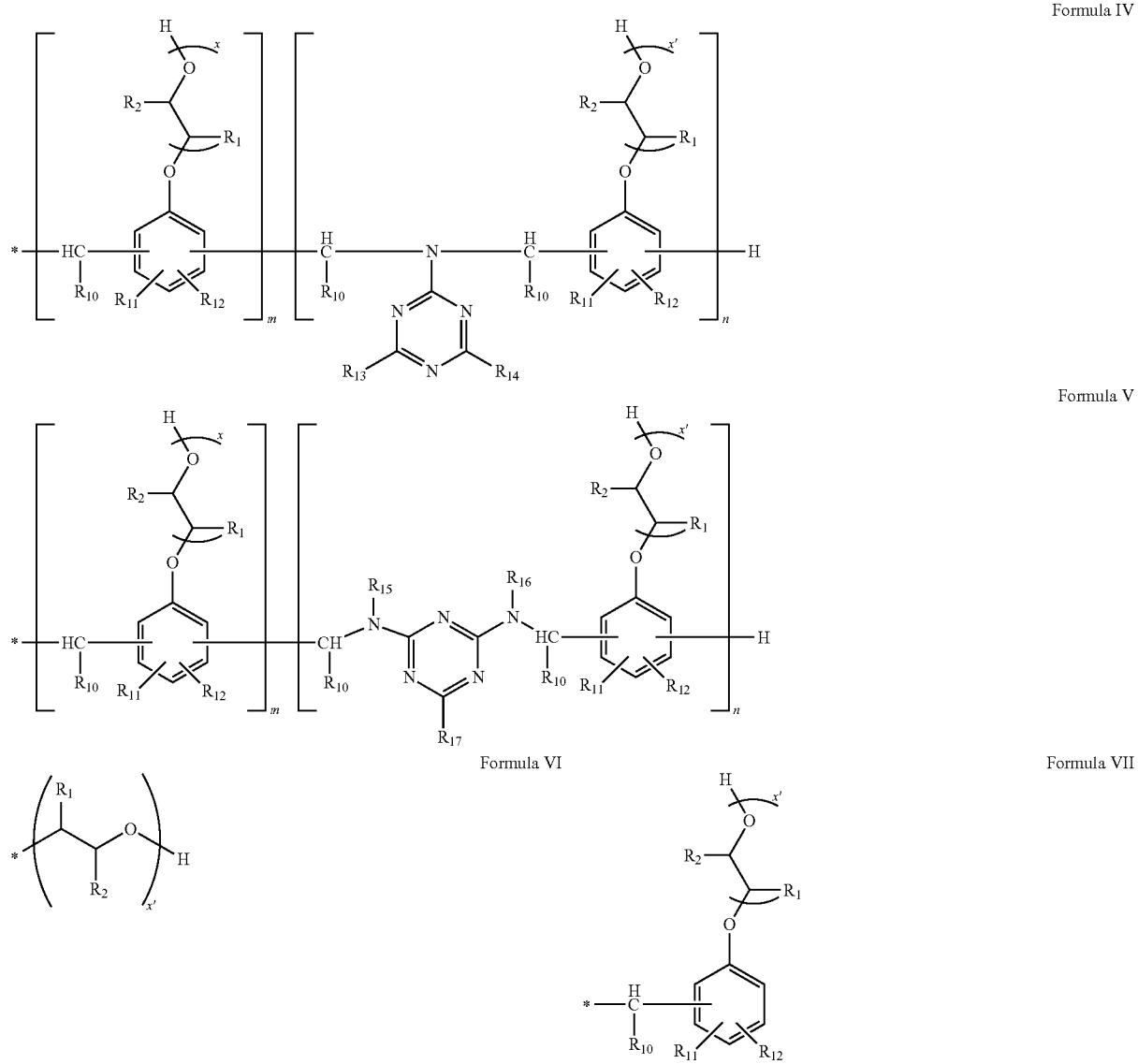

In the above Formulas, $R_1$ and $R_2$ are independently a hydrogen atom, an alkyl group having 1 to 4 carbon atoms, a vinyl group, or an alkyl group with 1 to 4 carbon atoms containing a hydroxyl group.

$R_{10}$ can be a hydrogen atom, an alkyl group with 1 to 10 carbon atoms, an alkyl group with 1 to 10 carbon atoms containing a hydroxyl group, a phenyl group, a vinyl group, a propenyl group, a hydroxyl-containing phenyl group, a pyrrole group, or a furanyl group.

$R_{11}$ and $R_{12}$ are each independently a hydrogen atom, an alkyl group with 1 to 10 carbon atoms, an alkoxy group having 1 to 10 carbon atoms, a phenyl group, a hydoxybenzene group, or an alkyl group with 1 to 10 carbon atoms with at least one carbon substituted with i) a hydroxyl group, ii) a hydroxybenzene group or iii) a phenyl group. In various embodiments, $R_{11}$ and $R_{12}$ can jointly form a common aromatic ring with or without a hydroxyl group.

$R_{13}$ and $R_{14}$ are each independently a hydrogen atom, an alkyl group with 1 to 10 carbon atoms, a vinyl group, a phenyl group, a hydroxyphenyl group, —NH(Formula VI), —N(Formula VI)$_2$, —NH(Formula VI), —N((Formula IV)(Formula VI)), —N(Formula VI)$_2$, or —NH$_2$.

$R_{15}$, $R_{16}$, and $R_{17}$ are each independently a hydrogen atom, an alkyl group with 1 to 10 carbon atoms, a vinyl group, a phenyl group, a hydroxyphenyl group, —NH(Formula VI), —N(Formula VI)$_2$, —NH(Formula VII), —N(Formula VI)(Formula VII), —N(Formula VII)$_2$, or —NH$_2$.

In the Formulas above, each m is independently from 1 to 10, each n is independently from 0 to 10, each x is independently from 1 to 2, and each x' is independently from 0 to 2. Monomers depicted by m and n can be arranged in any order, combination, or sub-combination.

The alkoxylated triazine-arylhydroxy-aldehyde condensates generally have a nitrogen content of from 0.5 weight percent to 40 weight percent, and from 5 weight percent to 15 weight percent in various other embodiments.

One example of the alkoxylated triazine-arylhydroxyaldehyde condensate is represented by Formula VII, below:

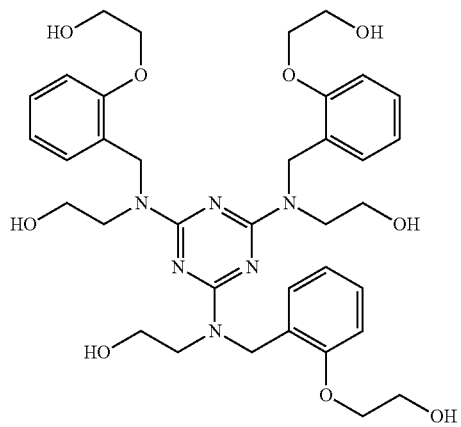

Formula VII

Another example of the alkoxylated triazine-arylhydroxyaldehyde condensate is represented by Formula IX, below:

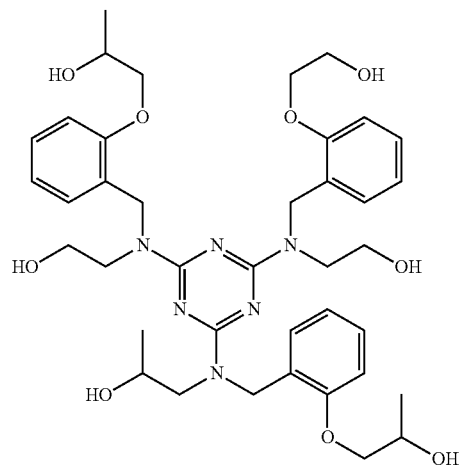

Formula IX

Another example of the alkoxylated triazine-arylhydroxyaldehyde condensate is represented by Formula X, below:

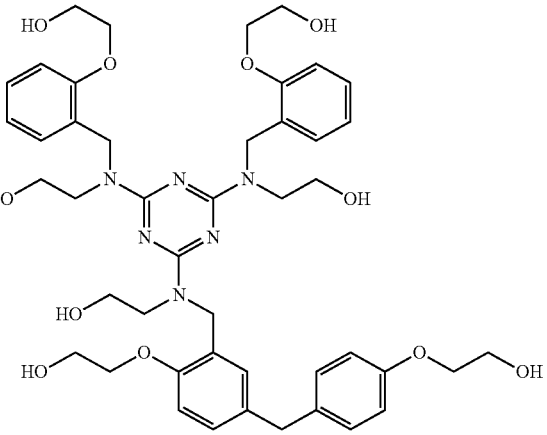

Formula X

Another example of the alkoxylated triazine-arylhydroxyaldehyde condensate is represented by Formula XI, below:

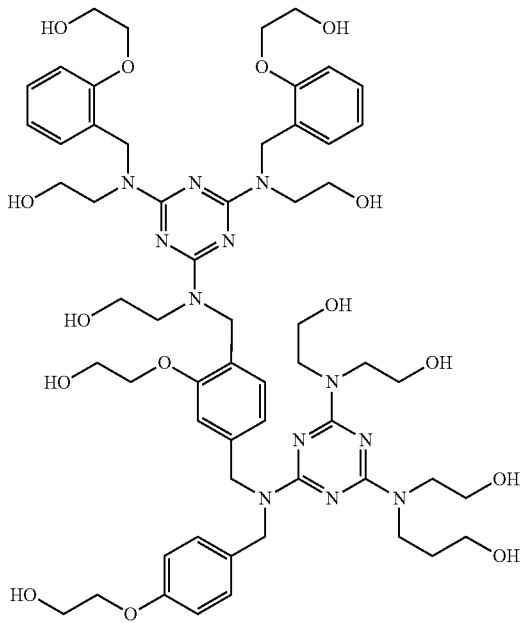 [SMILES: OCCCN(CCO)c1nc(N(CCO)CCO)nc(N(Cc2ccc(OCCO)cc2)Cc2ccc(CN(CCO)c3nc(N(CCO)Cc4ccccc4OCCO)nc(N(CCO)Cc4ccccc4OCCO)n3)c(OCCO)c2)n1]

Another example of the alkoxylated triazine-arylhydroxyaldehyde condensate is represented by Formula XII, below:

Formula XII

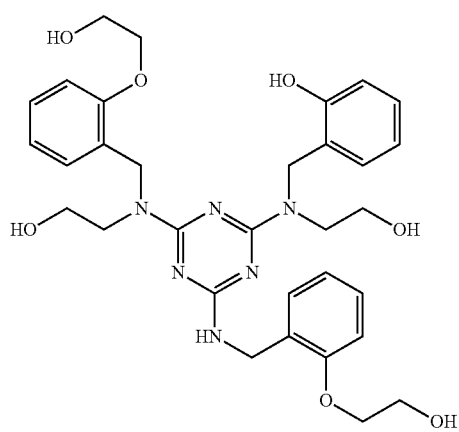

Another example of the alkoxylated triazine-arylhydroxy-aldehyde condensate is represented by Formula XIII, below:

Formula XIII

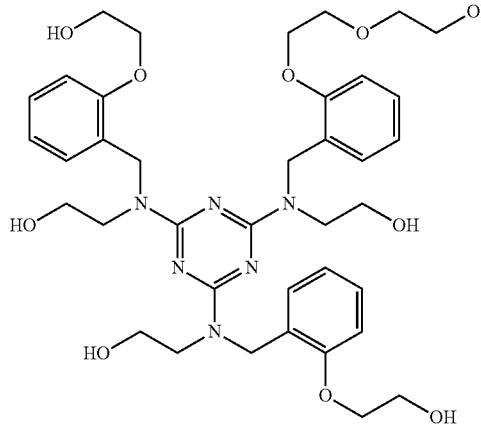

Another example of the alkoxylated triazine-arylhydroxy-aldehyde condensate is represented by Formula XIV, below:

Formula XIV

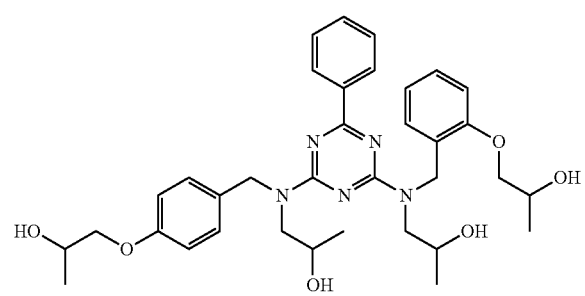

Another example of the alkoxylated triazine-arylhydroxy-aldehyde condensate is represented by Formula XV, below:

Formula XV

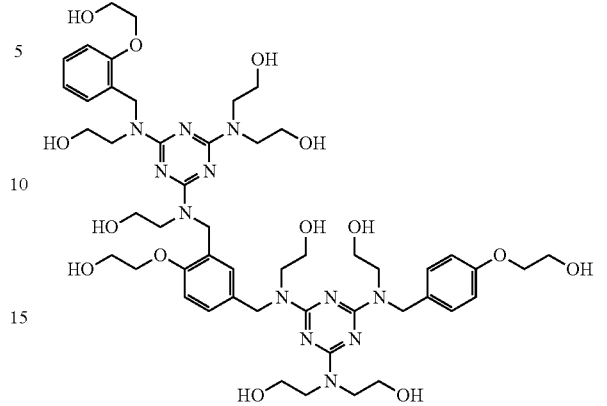

Another example of the alkoxylated triazine-arylhydroxy-aldehyde condensate is represented by Formula XVI, below:

Formula XVI

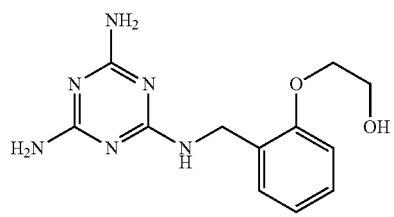

The alkoxylated triazine-arylhydroxy-aldehyde condensates of this invention generally have a viscosity in a solvent in the range of from about 1 Pascal second to 1,700 Pascal seconds at 25° C. Any and all ranges within 1 to 1,700 Pascal seconds are included herein and disclosed herein, for example, the alkoxylated triazine-arylhydroxy-aldehyde condensates in solvents can have a viscosity in the range of from 10 to 1,500 Pascal seconds or from 100 to 1,000 Pascal seconds at 25° C.

The alkoxylated triazine-arylhydroxy-aldehyde condensates of this invention can be used as polyisocyanate-reactive compounds to make polyurethanes and polyisocyanurate-based polymers.

In various embodiments, a reaction mixture is formed with at least one alkoxylated triazine-arylhydroxy-aldehyde condensate and at least one polyisocyanate. Examples of polyisocyanates that can be used include, but are not limited to m-phenylene diisocyanate, toluene-2,4-diisocyanate, toluene-2,6-diisocyanate, hexamethylene-1,6-diisocyanate, tetremethylene-1,4-diisocyanate, cyclohexane-1,4-diisocyanate, hexahydrotoluene diisocyanate, naphthylene-1,5-diisocyanate, methoxyphenyl-2,4-diisocyanate, diphenylmethane-4,4'-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dimethyldiphenylmethane-4,4'-diisocyanate, 4,4',4''-triphenyl methane triisocyanate, a polymethylene polyphenylisocyanate, polymeric diphenylmethane diisocyanate (PMDI), isophorone diisocyanate, toluene-2,4,6-triisocyanate and 4,4'-dimethyldiphenylmethane-2,2',5,5'-tetraisocyanate. In various embodiments, the polyisocyanate is diphenylmethane-4,4'-diisocyanate, diphenylmethane-2,4-diisocyanate, hexamethylene-1,6-diisocyanate, isophorone diisocyanate, toluene-2,4-diisocyanate, toluene-2,6-diisocyanate or mixtures thereof. Diphenylmethane-4,4'-diisocyanate, diphenylmethane-2,4-diisocyanate and mixtures thereof are generically referred to as MDI and all can be used. Toluene-2,4-diisocyanate, toluene-2,6-diisocyanate and mixtures thereof are generically referred to as TDI and all can be used.

Any of the foregoing polyisocyanates can be modified to include urethane, urea, biuret, carbodiimide, allophonate, uretonimine, isocyanurate, amide, or like linkages. Examples of modified isocyanates of these types include various urethane group and/or urea group-containing prepolymers and so-called 'liquid MDI' products and the like.

In various embodiments, the polyisocyanate can be a blocked isocyanate, where a standard polyisocyanate is prereacted with a blocking agent containing active hydrogen groups, which can then be deblocked at temperatures greater than 40° C. (typically in the range of from 100° C. to 190° C.). Examples of blocking agents include, but are not limited to γ-caprolactam, phenol, methyl ketone oxime, 1,2,4-triazole, and dimethyl malonate.

Polyols which can be used in conjunction with the alkoxylated triazine-arylhydroxy-aldehyde condensate include polyether polyols. These are prepared by polymerizing an alkylene oxide onto an initiator compound that has multiple active hydrogen atoms. Suitable initiator compounds include, but are not limited to alkylene glycols, glycol ethers, glycerine, trimethylolpropane, sucrose, glucose, fructose, ethylene diamine, hexamethylene diamine, diethanolamine, monoethanolamine, piperazine, aminoethylpiperazine, diisopropanolamine, monoisopropanolamine, methanol amine, dimethanol amine, and toluene diamine.

Polyester polyols can also be used as part of the isocyanate-reactive compound. Polyester polyols include reaction products of polyols, usually diols, with polycarboxylic acids or their anhydrides, usually dicarboxylic acids or dicarboxylic acid anhydrides. The polycarboxylic acids or anhydrides can be aliphatic, cycloaliphatic, aromatic, and/or heterocyclic.

Mannich base polyols, which are synthesized from Mannich bases, can also be used as part of the isocyanate-reactive compound.

In various embodiments, the alkoxylated triazine-arylhydroxy-aldehyde condensate is present in the isocyanate-reactive compound in a range of from about 5 weight percent to about 50 weight percent. Any and all ranges between 5 and 50 weight percent are included herein and disclosed herein; for example, the alkoxylated triazine-arylhydroxy-aldehyde condensate can be present in the isocyanate-reactive compound in a range of from 5 weight percent to 35 weight percent, from 15 weight percent to 25 weight percent, or from 9 weight percent to 21 weight percent.

In various embodiments, the alkoxylated triazine-arylhydroxy-aldehyde condensate can also act as a catalyst. Therefore, no extra catalyst is necessary for the reaction of the alkoxylated triazine-arylhydroxy-aldehyde condensate and polyisocyanate compound.

Optionally, in various embodiments, the polyisocyanate and alkoxylated triazine-arylhydroxy-aldehyde condensate mixture can also include a catalyst. Examples of catalysts include, but are not limited to tertiary amines such as dimethylbenzylamine, 1,8-diaza(5,4,0)undecane-7, pentamethyldiethylenetriamine, dimethylcyclohexylamine, and triethylene diamine. Potassium salts such as potassium acetate and potassium octoate can also be used as catalysts. In various embodiments, the alkoxylated triazine-arylhydroxyl-aldehyde condensate can also act as a catalyst.

In various embodiments, the alkoxylated triazine-arylhydroxy-aldehyde condensate also contains a diluent. Examples of diluents include, but are not limited to polyglycols such as ethylene glycol, glycerol, or diethylene glycol, etherified polyglycols such as monomethyl ether of ethylene glycol or dimethyl ether of ethylene glycol, and dibasic esters of acids such as diethyl adipate, dimethyl adipate, diethyl succinate, or dimethyl succinate. Mixtures of any of these diluents can also be used.

Depending upon the particular type of polymer being produced and the necessary attributes of the polymer, a wide variety of additional materials can be present during the reaction of the polyisocyanate compound with the alkoxylated triazine-arylhydroxy-aldehyde condensate. These materials include but are not limited to surfactants, blowing agents, cell openers, fillers, pigments and/or colorants, desiccants, reinforcing agents, biocides, preservatives, antioxidants, flame retardants, and the like.

If a flame retardant is included, the flame retardant is can be a phosphorus-containing flame retardant. Examples of phosphorus-containing flame retardants include, but are not limited to triethyl phosphate (TEP), triphenyl phosphate (TPP), trischloropropylphosphate, dimethylpropanephosphate, resorcinol bis(diphenylphosphate) (RDP), bisphenol A diphenyl phosphate (BADP), and tricresyl phosphate (TCP), dimethyl methylphosphonate (DMMP), diphenyl cresyl phosphate and aluminium diethyl phosphinate.

The relative amounts of polyisocyanate and alkoxylated triazine arylhydroxy aldehyde condensate are selected to produce a polymer. The ratio of these components is generally referred to as the 'isocyanate index' which means 100 times the ratio of isocyanate groups to isocyanate-reactive groups provided by the alkoxylated triazine-arylhydroxy-aldehyde condensate. The isocyanate index is generally at least 50 and can be up to 1000 or more. Rigid polymers such as structural polyurethanes and rigid foams are typically made using an isocyanate index of from 90 to 200. When flexible or semi-flexible polymers are prepared, the isocyanate index is generally from 70 to 125. Polymers containing isocyanurate groups are often made at isocyanate indices of at least 150, up to 600 or more.

To form the polymer, the polyisocyanate compound and the alkoxylated triazine-arylhydroxy-aldehyde condensate are mixed and cured. The curing step is achieved by subjecting the reaction mixture to conditions sufficient to cause the polyisocyanate compound and alkoxylated triazine-arylhydroxy-aldehyde condensate to react to form the polymer.

The polymer formed by the process of this invention can generally have a burn rate in the range of from 50 percent to 60 percent lower than a polyurethane composition that was not prepared with an alkoxylated triazine-arylhydroxy-aldehyde condensate. The polymer can also have a weight retention after burning in the range of from 70 percent to 115 percent higher, than a polyurethane composition that was not prepared with an alkoxylated triazine-arylhydroxy-aldehyde condensate. Additionally, the polymer can have a compressive strength at yield in the range of from 25 percent to 60 percent higher than a polyurethane composition that was not prepared with an alkoxylated triazine-arylhydroxy-aldehyde condensate.

A wide variety of polymers can be made in accordance with the invention through the proper selection of particular alkoxylated-triazine-arylhydroxy-aldehyde condensates, particular polyisocyanates, the presence of optional materials as described below, and reaction conditions. The process of the invention can be used to produce polyurethane and/or polyisocyanurate polymers of various types, including polyurethane foams, sealants and adhesives (including moisture-curable types), hot-melt powders, wood binders, cast elastomers, flexible or semi-flexible reaction injection molded parts, rigid structural composites, flexible polyurethane foams, binders, cushion and/or unitary backings for carpet and other textiles, semi-flexible foams, pipe insulation, automotive cavity sealing, automotive noise and/or vibration dampening, microcellular foams such as shoe soles, tire fillers and the like. These polymers can then be used to manufacture articles.

EXAMPLES

The triazine-arylhydroxy-aldehyde condensates used in Examples 1-8 can be represented as in Formulas XVII and XVIII, below:

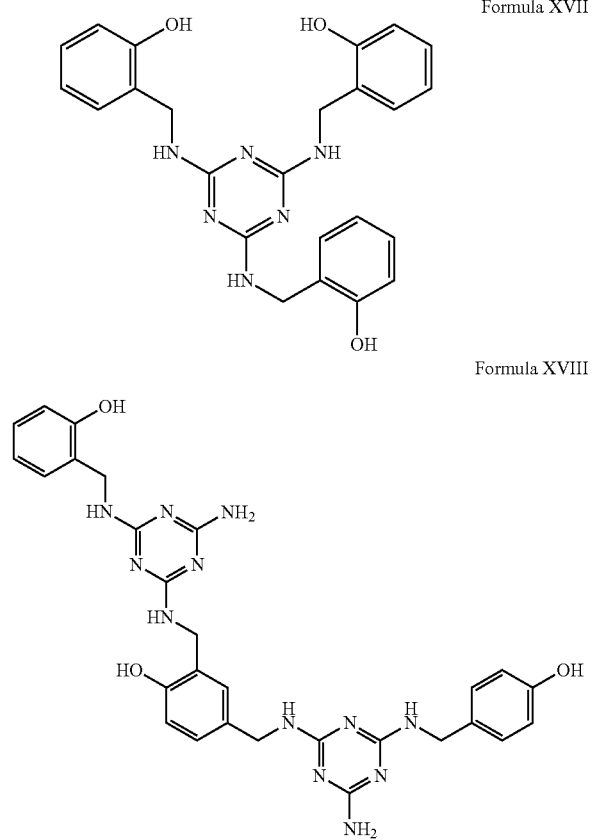

Formula XVII

Formula XVIII

These compositions were prepared using methods described in U.S. Pat. No. 9,249,251. Yield is calculated as the total sum of weight added to the flask minus the total weight of $CO_2$ expected to be lost.

Example 1

103 grams of triazine-arylhydroxy-aldehyde condensate, 88 grams of ethylene carbonate, and 4 g potassium carbonate were charged to a 250 mL 3 necked round bottom flask equipped with mechanical agitator, reflux condenser, thermocouple, and thermocouple controlled heating mantle. The mixture was heated to 160° C. and was held for 4-6 hours or until evolution of $CO_2$ had ceased and was then vacuum distilled to remove water. The yield was 95%.

Example 2

103 grams of triazine-arylhydroxy-aldehyde condensate and 88 grams of ethylene carbonate were charged to a 250 mL 3 necked round bottom flask equipped with mechanical agitator, reflux condenser, thermocouple, and thermocouple controlled heating mantle. The mixture was heated to 160° C. and was held for 4-6 hours or until evolution of $CO_2$ had ceased and was then vacuum distilled to remove water. The yield was 95%.

Example 3

103 grams of triazine-arylhydroxy-aldehyde condensate were charged to a 250 mL 3 necked round bottom flask equipped with mechanical agitator, reflux condenser, thermocouple, and thermocouple controlled heating mantle. The triazine-arylhydroxy-aldehyde condensate was heated to 160° C. and 88 grams of ethylene carbonate was fed to the flask over a period of 1 hour. The mixture was then held at a temperature of 160° C. for 4-6 hours or until the evolution of $CO_2$ had ceased. It was then vacuum distilled to remove water. The yield was 95%.

Example 4

103 grams of triazine-arylhydroxy-aldehyde condensate were charged to a 250 mL 3 necked round bottom flask equipped with mechanical agitator, reflux condenser, thermocouple, and thermocouple controlled heating mantle. After the triazine-arylhydroxy-aldehyde condensate was heated to 160° C., 44 grams of ethylene carbonate was fed to the flask over a period of 1 hour. The mixture was then held at a temperature of 160° C. for 4-6 hours until the evolution of $CO_2$ had ceased. It was then vacuum distilled to remove water. The yield was 95%.

Example 5

103 grams of triazine-arylhydroxy-aldehyde condensate were charged to a 250 mL 3 necked round bottom flask equipped with mechanical agitator, reflux condenser, thermocouple, and thermocouple controlled heating mantle. After the triazine-arylhydroxy-aldehyde condensate was heated to 160° C., 102 grams of propylene carbonate was fed to the flask over a period of 1 hour. The mixture was then held at a temperature of 160° C. for 4-6 hours until the evolution of $CO_2$ had ceased. It was then vacuum distilled to remove water. The yield was 95%.

Example 6

828 grams of triazine-arylhydroxy-aldehyde condensate was charged to a 3 L 4 necked round bottom flask equipped with mechanical agitator, reflux condenser, thermocouple, and thermocouple controlled heating mantle and heated to 160° C. Then 408 grams of propylene carbonate and 352 g of ethylene carbonate were fed over 1 hour as a mixture to the molten triazine-arylhydroxy-aldehyde condensate. The mixture was then held at a temperature of 160° C. for 4-6 hours or until evolution of $CO_2$ had ceased. The mixture was then vacuum distilled to remove any remaining volatiles or trace water. The yield was 95%.

Example 7

828 grains of triazine-arylhydroxy-aldehyde condensate and 3.5 grams of potassium carbonate were charged to a 3

L 4 necked round bottom flask equipped with mechanical agitator, reflux condenser, thermocouple, and thermocouple controlled heating mantle and heated to 160° C. Then 408 grams of propylene carbonate and 352 grams of ethylene carbonate were fed over 1 hour as a mixture to the molten triazine-arylhydroxy-aldehyde condensate. The mixture was then held at a temperature of 160° C. for 4-6 hours or until evolution of $CO_2$ had ceased. 7 grams of salicylic acid was then charged, and mixing continued for 10 minutes. The mixture was then vacuum distilled to remove water. The yield was 95%.

Example 8

240 grams of triazine-arylhydroxy-aldehyde condensate and 1.5 grams of potassium carbonate were charged to a 1 L 4 necked round bottom flask equipped with mechanical agitator, reflux condenser, thermocouple, and thermocouple controlled heating mantle and heated to 160° C. Then 204 grams of propylene carbonate and 176 grams of ethylene carbonate were fed over 1 hour as a mixture to the molten triazine-arylhydroxy-aldehyde condensate. The mixture was then held at a temperature of 160° C. for 4-6 hours or until evolution of $CO_2$ had ceased. 3 grams of salicylic acid was charged to the reaction mixture, and mixing continued for 10 minutes. The mixture was then vacuum distilled to remove water. The yield was 95%.

Example 9

The alkoxylated triazine-arylhydroxy-aldehyde condensate from Example 3 was flaked and fed into a grinding mill and an amount of methylene diphenyl diisocyanate was also fed to achieve a desired isocyanate ratio of 1:1 based on the hydroxyl equivalent weight of the triazine-arylhydroxy-aldehyde condensate. The composition was ground to a mesh size of 50-100% through 200 mesh. The powdered composition was cured above the melting point or softening point of the resulting mixture to yield a cross-linked polyurethane.

Example 10

20 grams of alkoxylated triazine-arylhydroxy-aldehyde condensate from Example 4 were dissolved in 20 grams of triethyl phosphate and 10 grams of ethylene glycol to yield a viscous solution with an approximate hydroxyl equivalent weight of 98. This mixture was further formulated with cyclopentane as a surfactant and emulsified. A polymeric isocyanate was added to achieve a specific isocyanate ratio of 1:1 and then mixed to create a polyurethane foam.

Example 11: Viscosities of Alkoxylated Triazine-Arylhydroxy-Aldehyde Condensates An ARES-G2 rheometer (TA Instruments) equipped with stainless steel parallel plates was operated under rotational mode to determine the viscosities of the formulation from Example 3 at 150° C., 140° C., and 130° C. The viscosity was determined from a "zero-shear" approximation in which the viscosity is measured as a function of shear rate (0.1-100 l/s). The zero shear viscosity was determined by averaging the viscosity in the Newtonian region, which is approximately 1-100 l/s. Ten data points were measured for every magnitude change of shear rate such as 10 points between 0.1 and 1 l/s. The lower temperature was determined when the materials exhibited non-Newtonian behavior such as shear thinning. The viscosity of triazine-arylhydroxy-aldehyde condensate was compared with the viscosity of ethoxylated triazine-arylhydroxy-aldehyde condensate. Results are shown in Table 1 for Examples 3, 5, and 8, below.

TABLE 1

Viscosity Results

| Temperature (° C.) | Viscosity of Triazine Arylhydroxy-Aldehyde Condensate (Pa · s) | Viscosity of Alkoxylated Triazine Arylhydroxy-Aldehyde Condensate From Example 3 (Pa · s) | Viscosity of Alkoxylated Triazine Arylhydroxy-Aldehyde Condensate From Example 8 (Pa · s) | Viscosity of Alkoxylated Triazine Arylhydroxy-Aldehyde Condensate From Example 5 (Pa · s) |
|---|---|---|---|---|
| 150 | 6.0 | 0.18 | 0.013 | 0.048 |
| 140 | 23 | 0.32 | 0.022 | 0.092 |
| 130 | 117 | 0.65 | .041 | 0.112 |

Alkoxylated triazine-arylhydroxy-aldehyde condensates were also dissolved in solvents after which viscosity was measured using the method described above. Tables 2, 3, and 4 show viscosity results for samples at 50° C., 40° C., 30° C., and 25° C.

TABLE 2

Viscosity Results for Example 3 in Diethylene Glycol (DEG)

| % DEG | Viscosity at 50° C. (Pa · s) | Viscosity at 40° C. (Pa · s) | Viscosity at 30° C. (Pa · s) | Viscosity at 25° C. (Pa · s) |
|---|---|---|---|---|
| 20 | 5.62 | 18.14 | 77.64 | 168.09 |
| 31 | 0.75 | 1.78 | 4.98 | 8.45 |
| 40 | 0.33 | 0.71 | 1.74 | 2.77 |
| 50 | 0.15 | 0.27 | 0.58 | 0.95 |
| 61 | 0.07 | 0.11 | 0.21 | 0.31 |

TABLE 3

Viscosity Results for Example 8 in Triethyl Phosphate (TEP)

| % TEP | Viscosity at 50° C. (Pa · s) | Viscosity at 40° C. (Pa · s) | Viscosity at 30° C. (Pa · s) | Viscosity at 25° C. (Pa · s) |
|---|---|---|---|---|
| 22 | 2.49 | 8.22 | 30.05 | 71.06 |
| 31 | 0.64 | 1.68 | 4.96 | 9.68 |
| 41 | 0.13 | 0.26 | 0.56 | 0.89 |
| 51 | 0.04 | 0.06 | 0.09 | 0.13 |

TABLE 4

Viscosity Results for Example 8 in Diethylene Glycol (DEG)

| % DEG | Viscosity at 50° C. (Pa · s) | Viscosity at 40° C. (Pa · s) | Viscosity at 30° C. (Pa · s) | Viscosity at 25° C. (Pa · s) |
|---|---|---|---|---|
| 17 | 28.28 | 133.19 | 888.13 | 1641.36 |
| 25 | 5.13 | 17.50 | 72.94 | 156.06 |
| 50 | 0.13 | 0.26 | 0.54 | 0.92 |
| 40 | 0.42 | 0.97 | 2.64 | 4.44 |
| 30 | 0.94 | 2.41 | 7.46 | 13.52 |

Based upon the results of Tables 1-4, an alkoxylated triazine-arylhydroxy-aldehyde condensate can be used as a rheology modifier for polyurethane crosslinking systems.

Example 12: Effect of Introducing Alkoxylated Triazine-Arylhydroxy-Aldehyde Condensate Into a typical PU Formulation for Rigid Foams As a first step, a reference polyurethane mixture (Reference Formulation #1) and test polyurethane mixtures (Test Formulations #1 and #2) were prepared using the two formulations shown in Table 5, below. The alkoxylated triazine-arylhydroxy-aldehyde condensate of the current invention was mixed into the reference carbohydrate-based aliphatic polyol (Reference Polyol #1) at a 80:20 ratio of Reference Polyol #1 to the ethoxylated condensate from Example 3 along with other components listed in the Table, at 100° C. in a cup at 2200 RPM using Speed Mixer DAC 400 FV. To form Reference Formulation #1, Reference Polyol #1 was blended with other components in the same manner as described above. To form Test Formulation #2, Reference Polyol #1 was blended with a conventional aromatic-based polyol and the ethoxylated condensate of Example 3.

These polyol mixtures were then mixed with Rubinate M, a polyisocyanate, to an isocyanate index of 110% to form a free-rise foam. The actual mixing technique and equipment used are described below in detail under 'Method to Prepare Foam Samples for Flame and Mechanical Tests'. The reactivity differences between the two formulations are measured as the mix time, cream time, gel time, rise time and tack-free time as shown in Table 5.

Method to Prepare Foam Samples for Flame and Mechanical Tests

Foams were prepared using a high-torque mixer (CRAFTSMAN 10-Inch Drill Press, Model No. 137.219000) at 3,100 rpm speed. Polyol components and isocyanate components of the foam systems were mixed for 10 seconds. Afterwards, the mixture was transferred into an open cake box before the cream time and was allowed to rise. Two sets of foams were prepared using 50 grams and 100 grams of total polyols, respectively. Foams with 50 grams of total polyols were prepared by pouring the foaming mix into cake boxes of 6"×6"×3" dimensions and those with 100 grams of total polyols were prepared by pouring the mix into cake boxes of 12"×12"×4" dimensions. Foams prepared with 100 grams of total polyols were used for testing of density, flammability, and compressive strength properties and foams prepared with 50 grams were used for reactivity comparisons.

Description of Materials:

Dabco® DC193, a silicone surfactant available from Evonik.

Dabco® 33LV, an amine catalyst available from Evonik.

Niax A-1, a catalyst available from Momentive Performance Materials.

Rubinate® M, a polymeric MDI isocyanate, available from Huntsman.

TABLE 5

Properties of Formulations

| | Reference Formulation #1 | Test Formulation #1 | Test Formulation #2 |
|---|---|---|---|
| Ref Polyol #1 (carbohydrate-based aliphatic polyol), g | 100 | 80 | 70 |
| Ref Polyol #2 (aromatic polyol), g | 0 | 0 | 21 |
| Ethoxylated Triazine-arylhydroxy-aldehyde condensate, g | 0 | 20 | 9 |
| Water, g | 4.5 | 4.5 | 4.5 |
| Dabco DC193, g | 2 | 2 | 2 |
| Dabco 33LV, g | 1.8 | 1.8 | 1.8 |
| Niax A-1, g | 0.1 | 0.1 | 0.1 |
| Rubinate M, g | 172.99 | 176.03 | 182.16 |
| Residual water, g | 0.02 | 0.02 | 0.07 |
| Isocyanate Index | 110% | 110% | 110% |
| Reaction profile of free-rise foams | | | |
| Mix time, s | 10 | 10 | 10 |
| Cream time, s | 22 | 18 | 20 |
| Gel time, s | 67 | 43 | 45 |
| Rise time, s | 98 | 75 | 73 |
| Tack-free time, s | 116 | 78 | 75 |

Example 13: Fire Resistance and Mechanical Properties

Physical and Mechanical Property Testing Methods

Core Density, pcf Method: ASTM D 1622-03
Compressive Strength, psi: ASTM D 1621-00
Compressive Strain @ Yield %: ASTM D 1621-00
Flame Test: The burning rate and weight retention after burning were measured using a modified ASTM D 4986 flammability test. According to ASTM 4986, a specific burner is used and is defined by ASTM D5025 and a gas with a heat content of $37\pm1$ MJ/m$^3$. In the modified test herein, a Bernzomatic torch TS4000, which heats to 1982° C. in air was used. Specimen sizes and calculation of the burning rates are identical to the ASTM D 4986 method. The flame source is removed at the time when the flame reaches the first mark line on the specimen. According to ASTM D 4986, one set of five specimens are conditioned for at least 48 hours at 23° C. and relative humidity of 50±5% prior to testing. The second set of five specimens are conditioned in an air circulating oven for 168±2 h at 70±2° C., and then cooled in a desiccator for at least 4 hours at room temperature prior to testing. In the modified test, 6 specimens are cut prior to testing from foam aged at room conditions (ambient temperature and humidity) for a minimum of 7 days after preparation of the foam.

Table 6, below shows properties of foams prepared using three different formulations. One reference formulation used a carbohydrate-based aliphatic polyol. The two test formulations (#3 and #4) are prepared from various amounts of the carbohydrate-based aliphatic polyol, a conventional aromatic-based polyol, and the ethoxylated triazine-arylhydroxy-aldehyde condensate of Example 3. These formulations were prepared as described in Example 12, above.

As can be seen from Table 6, foams prepared from the alkoxylated triazine-arylhydroxy-aldehyde condensate provided slower burn rates, higher weight retentions, and good mechanical properties. The compressive strength at yield and the compressive strength at maximum load significantly increased with the introduction of the alkoxylated triazine-arylhydroxy-aldehyde condensate into the formulation. In general, the compressive strength is dependent on the foam density. However, this increase in the compressive strength with introduction of alkoxylated triazine-arylhydroxy-aldehyde condensate into the formulation is much greater than the possible effect of an increase in the foam density. The compressive strengths at yield and at maximum load of foams containing alkoxylated triazine-arylhydroxy-aldehyde condensate, when normalized to the density of the reference foam of 1.98 pcf, are significantly higher than that of the reference foams. Therefore, the observed effect of alkoxylated triazine-arylhydroxy-aldehyde condensates on compressive strength is significant.

It is important to note that the compressive strain at yield was not affected significantly with the introduction of the alkoxylated triazine-arylhydroxy-aldehyde condensate, which indicates the overall rigidity (friability) of the foams was not significantly affected.

As can be seen in both Tables 5 and 6, polymers prepared with alkoxylated triazine-arylhydroxy-aldehyde condensates have cream times that are about 4 to 19 percent lower, gel times that are about 35 to 42 percent lower, rise times that are about 23 to 34 percent lower, and tack-free times that are about 32 to 43 percent lower than the reference formulation that was not prepared with an alkoxylated triazine-arylhydroxy-aldehyde condensate. This indicates that foams prepared from the alkoxylated triazine-arylhydroxy-aldehyde condensate have higher reactivites than the foam prepared from the reference formulation.

As can be seen in Table 6, as the quantity of the alkoxylated triazine-arylhydroxy-aldehyde condensate component in the formulations increased from 0% to 15% and then to 21%, the burn rate continued to drop further and the weight retention increased, which indicates superior fire retardant characteristics when compared the to the reference formulation. The superior fire retardant characteristics of alkoxylated triazine-arylhydroxy-aldehyde condensates of this invention are attributed to its relatively high nitrogen and aromatic content.

These results show the effectiveness of the alkoxylated triazine-arylhydroxy-aldehyde condensates of the current invention as flame retardants in polyurethane rigid foam formulations and their potential use in other polyurethane applications as well.

TABLE 6

Mechanical and Flame Properties of Reference vs. Test Formulations

|  | Reference PU Formulation #1 | Test PU Formulation #3 | Test PU Formulation #4 |
|---|---|---|---|
| Ref Polyol #1-carbohydrate-based aliphatic polyol, g | 100 | 50 | 30 |
| Ref Polyol #2-aromatic polyol, g | 0 | 35 | 49 |
| Ethoxylated triazine-arylhydroxy-aldehyde condensate, g | 0 | 15 | 21 |
| Water, g | 4.5 | 4.5 | 4.5 |
| Dabco DC193, g | 2.0 | 2.0 | 2.0 |
| Dabco 33LV, g | 1.8 | 1.8 | 1.8 |
| Niax A-1, g | 0.1 | 0.1 | 0.1 |
| Rubinate M, g | 172.99 | 187.79 | 193.43 |
| Residual water, g | 0.02 | 0.11 | 0.14 |
| Isocyanate Index | 110% | 110% | 110% |
| Density, pcf | 1.98 ± 0.01 | 2.17 ± 0.05 | 2.37 ± 0.06 |
| Mix time, s | 10 | 10 | 10 |
| Cream time, s | 22 | 19 | 21 |
| Gel time, s | 67 | 41 | 39 |
| Rise time, s | 98 | 68 | 65 |
| Tack-free time, s | 116 | 70 | 67 |
| Compressive Strength at Yield, psi | 24.4 ± 1.8 | 30.8 ± 2.2 | 39.0 ± 2.7 |
| Compressive Strain at Yield, % | 6.9 ± 2.6 | 5.8 ± 0.7 | 9.1 ± 2.7 |
| Normalized Compressive Stress at Yield to a Density of 1.98 pcf, psi | 24.4 ± 1.8 | 28.1 ± 2.0 | 32.6 ± 2.3 |
| Normalized Compressive Stress at Maximum Load to a Density of 1.98 pcf, psi | 24.9 ± 1.4 | 28.4 ± 2.2 | 33.9 ± 3.5 |
| Burn Rate, cm/min | 29.6 ± 1.8 | 14.0 ± 0.4 | 12.1 ± 0.5 |
| Weight Retention, % | 38.2 ± 5.6 | 66.5 ± 7.4 | 80.4 ± 3.9 |
| Change in Burning Rate | n/a | −52.70% | −59.10% |
| Change in Weight Retention | n/a | 74.10% | 110.50% |

The invention claimed is:

1. A process comprising:
    forming a reaction mixture containing at least one polyisocyanate and an isocyanate-reactive compound comprising at least one alkoxylated triazine-arylhydroxy-aldehyde condensate composition
    wherein the alkoxylated triazine-arylhydroxy-aldehyde condensate composition is a reaction product of a triazine-arylhydroxy-aldehyde condensate and at least one alkylene carbonate.

2. A process in accordance with claim 1 further comprising curing the reaction mixture to form a polymer.

3. The process of claim 1 wherein the reaction mixture further comprises a phosphorus-containing flame retardant.

4. The process of claim 1 wherein the isocyanate-reactive compound further comprises a diluent selected from the group consisting of ethylene glycol, glycerol, diethylene glycol, monomethyl ether of ethylene glycol, dimethyl ether of ethylene glycol, diethyl adipate, dimethyl adipate, diethyl succinate, dimethyl succinate and combinations thereof.

5. The process of claim 1 wherein the polyisocyanate is selected from the group consisting of diphenylmethane-4,4'-diisocyanate (4,4 MDI), diphenylmethane-2,4'-diisocyanate (2,4 MDI), toluene-2,4-diisocyanate, toluene-2,6-diisocyanate, isophorone diisocyanate, hexamethylene-1,6-diisocyanate, polymeric diphenylmethane diisocyanate (PMDI) and combinations thereof.

6. The process of claim 1 wherein the polyisocyanate is a blocked isocyanate.

7. The process of claim 2 wherein the polymer is prepared with an isocyanate-reactive compound having from 9 weight percent to 21 weight percent of the alkoxylated triazine-arylhydroxy-aldehyde condensate.

8. The process of claim 7 wherein the polymer has a cream time that is from 4 percent to 19 percent lower than a polymer that was not prepared with an alkoxylated triazine-arylhydroxy aldehyde condensate.

9. The process of claim 7 wherein the polymer has a gel time that is from 32 percent to 42 percent lower than a polymer that was not prepared with an alkoxylated triazine-arylhydroxy aldehyde condensate.

10. The process of claim 7 wherein the polymer has a rise time that is from 23 percent to 34 percent lower than a polymer that was not prepared with an alkoxylated triazine-arylhydroxy aldehyde condensate.

11. The process of claim 7 wherein the polymer has a tack-free time that is from 32 percent to 43 percent lower than a polymer that was not prepared with an alkoxylated triazine-arylhydroxy aldehyde condensate.

12. The process of claim 7 wherein the polymer has a burn rate in the range of from 50 percent to 60 percent lower than a polyurethane composition that was not prepared with an alkoxylated triazine-arylhydroxy-aldehyde condensate.

13. The process of claim 7 wherein the polymer has a weight retention after burning in the range of from 70 percent to 115 percent higher than a polyurethane composition that was not prepared with an alkoxylated triazine-arylhydroxy-aldehyde condensate.

14. The process of claim 7 wherein the polymer has a compressive strength at yield in the range of from 25 percent to 60 percent higher than a polyurethane composition that was not prepared with an alkoxylated triazine-arylhydroxy-aldehyde condensate.

15. The process of claim 2 wherein the polymer is a polyurethane or polyisocyanurate foam.

16. The process of claim 2 wherein the polymer is a wood binder.

17. An article prepared from the polyurethane or polyisocyanurate foam of claim 15.

18. An article prepared from the wood binder of claim 16.

19. An article prepared from the process of claim 6.

* * * * *